(12) United States Patent
Zhou et al.

(10) Patent No.: US 11,600,958 B2
(45) Date of Patent: Mar. 7, 2023

(54) SENSING COMPONENT AND INTELLIGENT SOCKET

(71) Applicant: Xindongzhen (Suzhou) Intelligent Technology Co., Ltd., Suzhou (CN)

(72) Inventors: Changgeng Zhou, Suzhou (CN); Zhibin Zhou, Suzhou (CN)

(73) Assignee: Xindongzhen (Suzhou) Intelligent Technology Co., Ltd., Suzhou (CN)

( * ) Notice: Subject to any disclaimer, the term of this patent is extended or adjusted under 35 U.S.C. 154(b) by 185 days.

(21) Appl. No.: 16/826,388

(22) Filed: Mar. 23, 2020

(65) Prior Publication Data

US 2020/0235532 A1 Jul. 23, 2020

(30) Foreign Application Priority Data

Jan. 21, 2019 (CN) .......................... 201920095065.7

(51) Int. Cl.
| | |
|---|---|
| *H01R 13/66* | (2006.01) |
| *H01R 13/717* | (2006.01) |
| *H01R 13/73* | (2006.01) |
| *H05K 7/14* | (2006.01) |
| *H01R 13/70* | (2006.01) |

(52) U.S. Cl.
CPC ..... *H01R 13/6683* (2013.01); *H01R 13/6691* (2013.01); *H01R 13/70* (2013.01); *H01R 13/717* (2013.01); *H01R 13/73* (2013.01); *H05K 7/14* (2013.01)

(58) Field of Classification Search
CPC ........... H01R 13/6683; H01R 13/6691; H01R 13/70; H01R 13/717; H01R 13/73; H01R 24/78; H05K 7/14; G01N 33/0075
See application file for complete search history.

(56) References Cited

U.S. PATENT DOCUMENTS

| | | | | |
|---|---|---|---|---|
| 4,872,081 A | * | 10/1989 | Murphy | H01R 13/6666 361/117 |
| 5,485,356 A | * | 1/1996 | Nguyen | H01R 13/717 174/66 |
| 6,199,264 B1 | * | 3/2001 | Marcou | H01R 13/6666 29/593 |
| 6,423,900 B1 | * | 7/2002 | Soules | H01H 9/185 174/66 |
| 6,552,888 B2 | * | 4/2003 | Weinberger | H01R 13/713 361/57 |
| 9,030,789 B2 | * | 5/2015 | Benoit | H01R 25/00 361/42 |
| 9,070,272 B2 | * | 6/2015 | Gettings | G01N 33/0031 |
| 9,112,321 B2 | * | 8/2015 | Bhosale | H01R 13/717 |
| 9,460,645 B2 | * | 10/2016 | Braunstein | G09F 13/22 |
| 9,577,389 B2 | * | 2/2017 | Dicks | H01R 13/6683 |

(Continued)

*Primary Examiner* — Travis S Chambers
(74) *Attorney, Agent, or Firm* — Idea Intellectual Limited; Margaret A. Burke; Sam T. Yip (57) ABSTRACT

The present invention discloses a sensing component and an intelligent socket, comprising a sensing unit, a warning unit and a control unit; the sensing unit and the warning unit are connected to the control unit respectively; the sensing unit acquires the environmental data and sends the data to the control unit for processing and analysis; the control unit sends the control signal to the warning unit to execute. The intelligent socket also comprises the sensing component, a wireless communication and an indicator light unit.

14 Claims, 7 Drawing Sheets

(56) References Cited

U.S. PATENT DOCUMENTS

| | | | |
|---|---|---|---|
| 2012/0170292 A1* | 7/2012 | Bhosale | H01R 13/6658 |
| | | | 362/415 |
| 2015/0255932 A1* | 9/2015 | Dicks | H01R 13/6683 |
| | | | 307/326 |
| 2017/0324195 A1* | 11/2017 | Eriksen | H02H 9/042 |
| 2019/0020156 A1* | 1/2019 | Smith | G05F 3/02 |
| 2019/0221958 A1* | 7/2019 | Karc | H02G 3/121 |
| 2021/0249823 A1* | 8/2021 | Eriksen | H01R 24/78 |

* cited by examiner

SENSING COMPONENT AND INTELLIGENT SOCKET

CROSS-REFERENCE TO RELATED APPLICATION

This application claims priority from the Chinese Patent Application Number 2019200950657 filed on Jan. 21, 2019, and the disclosure of which is incorporated herein by reference in its entirety.

FIELD OF THE INVENTION

The present invention relates to the technical field of smart living. More particularly, it relates to a sensing component and an intelligent socket.

BACKGROUND

In recent years, with the continuous improvement of people's living standards, large-scale household appliances with high power and energy consumption, including air conditioning, television and refrigerator, have been popularized, and the power consumption of each family or enterprise is also rising. However, the existing socket products are only for securing power supply, and do not have the function to connect or cut off the circuit of the electrical work remotely, which limit the function of the socket. Therefore, the conventional sockets neither provide more functional supports to users nor maximize the efficiency of large household appliances; they even have problems such as energy waste and potential safety issues due to overuse of the electricity.

SUMMARY OF THE INVENTION

This section aims to summarize some aspects of the embodiments of the present invention and to briefly describe some preferred embodiments. The simplification or omission may be made in this section, the abstract of the specification, and the title to avoid obscuring the purpose of this section, the abstract of the specification, and the title. Such simplification or omission may not be used to limit the scope of the present invention.

In view of the above-mentioned technical drawbacks, one objective of the present invention is to provide an sensing component, which can collect environmental data, send out corresponding warnings according to data comparison, and control the switch of the electrical appliances.

Some advantages of the present invention: the intelligent socket includes a wireless communication and an indicator light unit to offer the sensing and interactive functions, making the socket more convenient, more intelligent, and improve the safety of the electrical appliance.

DETAILED DESCRIPTION

Example 1

Figure 1:
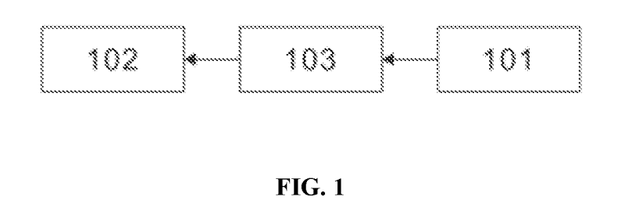
FIG. 1 is a schematic diagram depicting the overall working principle of the present sensing component.

The working principle of a sensing component 100 of the present invention is illustrated in FIG. 1, and the sensing component of the present invention is configured to monitor various environmental data from where the component is located, and generate corresponding responsive warnings. The sensing component 100 includes a sensing unit 101, a warning unit 102 and a control unit 103, wherein the sensing unit 101 acquires various environmental data such as temperature, humidity, sound or light, etc.; after the data acquisition, the data is sent to the control unit 103 for processing and analysis to generate the corresponding control signal; the warning unit 102 receives and executes the control signal sent by the control unit 103. The warning unit 102 is controlled by the control unit 103 to make a response action, and is configured to inform the normal or dangerous states through the comparison between the monitored data with the preset data including the display action under the normal state and the warning action under the abnormal state, in order to provide a favorable environment and improve the safety. Moreover, the sensing component 100 also includes the power supply required for the operation of the components, thus a power supply unit can be installed in the sensing component 100 to connect with each of the components for power supply.

Furthermore, the sensing unit 101 can include different sensors to form a combination of sensors. A sensor is a detection device, which can detect a measured signal and transform the measured signal into electrical signals or other required forms of output signals according to certain rules, so as to meet the requirements for signal transmission, processing, storage, display, recording and control. Generally, according to its basic sensing function, it can be divided into ten categories: heat-sensitive element, light-sensitive element, gas-sensitive element, force-sensitive element, magnetic-sensitive element, humidity-sensitive element, sound-sensitive element, radiation-sensitive element, color-sensitive element and taste-sensitive element. In one embodiment, it adopts temperature and humidity sensor, sound sensor, light sensor or carbon monoxide sensor to monitor and detect the temperature and humidity, sound, light and carbon monoxide in the environment, respectively, so as to provide a favorable and safe environment for users. The sensing unit 101 includes different sensors to form a combination of sensors, and the combination of various sensors is not limited. In order to save cost and reduce waste of components, the combination of various sensors in the sensing component 100 can vary according to the actual needs in different scenarios. For example, in the case where only light or temperature needs to be detected, the sensor combination in the sensing unit 101 includes temperature sensor and light sensor. In case where only carbon monoxide detection is needed, the sensor combination only consists of a carbon monoxide sensor, and so on.

The control unit 103 is a central processor, which is an integrated circuit component, responsible for the process management of the program, and is also a command control center, including an arithmetic logic unit, an instruction register, an instruction decoder and an operation controller, etc. The control unit is mainly responsible for decoding instructions, sending out control signals to complete each operation of each instruction, and sending them to corresponding components, so as to control these components to act according to the requirements of the instructions, which is very important in coordination of work in order. The control unit also has data processing function, which means it carries out arithmetic operation and logic operation or other data processing, and completes corresponding instruction control according to data analysis. For example, in one embodiment, the control unit 103 can be MCU, i.e. micro control unit, also known as single-chip microcomputer. The frequency and specification of MCU are reduced, and the space occupied by the peripheral interfaces of such as memory, counter, USB, A/D conversion, UART, PLC, DMA, etc., is also reduced appropriately. In addition to saving more space, the LCD drive circuit is integrated into a single chip to form a chip level computer, which can control different combinations for different applications, such as mobile phones, PC peripherals, remote controls, automotive electronics, industrial stepping motors, and robot arm control, etc. The sensing unit 101 and warning unit 102 are both connected with the micro control unit through wire connection.

Furthermore, the warning unit 102 including the indicator light unit 102a executes the control signal from the control unit 103. The indicator light unit 102a would emit warning light including different combinations of light color and brightness. When the user sees the light on, change in color or intensity of the light, it would inform the user whether the environmental data is normal or not by way of light indication. Moreover, some preset values can be input according to the user's needs. By comparing the detection value with the preset value, it can determine whether the light should be on, the color or the light intensity should be changed. It is very flexible, making it more suitable for users with different needs.

In addition, the warning unit 102 includes a speaker unit 102b, which can emit a warning sound with a warning light, and the emission of the warning sound and light can be set to be effected simultaneously or independently. Therefore, even when the user may not notice the warning light, the speaker unit sends out a warning sound to alert the user, or vice versa, so that it improves reliability and safety of the present invention. The user can set different sound effects of the warning sound of the sensing component 100 on a smart terminal or device according to his preference, such as 1-policecar, 2-incident, 3-countdown, 4-ghost, 5-sniperifle, 6-battle, 7-airraid, 8-bark, etc. When the abnormal state is detected in the monitoring part of the control unit 103, the alarm short message can be sent to the designated intelligent terminal by using the mobile network through the short message platform.

It should also be noted that the control unit 103 is respectively connected to the sensing unit 101 and the warning unit 102 to form an assembly of the component, and the connection mode can be a connection by circuit board or wire. The connection by circuit board refers to an assembly of different units on a circuit board through packaging to form a circuit. It also includes all kinds of other auxiliary elements and power supply elements required in the circuit. Reference is made to any implementation mode of the circuit board in the prior art, which will not be discussed in detail herein.

Figure 2:
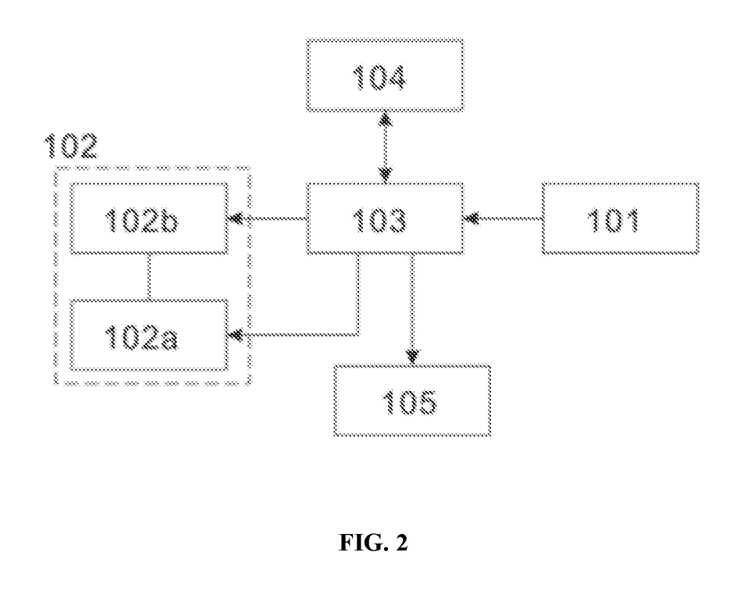
FIG. 2 is a schematic diagram depicting the overall working principle of the present sensing component including a wireless communication unit and a switch unit.

The sensing component 100 can also be connected to an external user smart terminal or device by means of certain communication to enable remote control and protection of the sensing component. The protection described herein refers to when the sensor of the sensing component 100 detects abnormality, the circuit on which the sensing component 100 effects is cut off. In various embodiments, the sensing component 100 further includes a wireless transmission unit 104 and a switch unit 105. More specifically, the wireless transmission unit 104 is connected to the control unit 103 and communicates with the user smart terminal or device through the wireless transmission mode. For example, connection to the user smart device such as mobile phone, tablet or computer can be made according to the communication protocols such as HTTP and MQTT through WI-FI™ and BLUETOOTH®. In order to save space, the wireless transmission unit 104 and the control unit 103 can be arranged in the same printed circuit board and connected through the printed circuit on the circuit board.

The user is able to set the preset value as the threshold of triggering the output signal through changing the default setting in the control unit 103, and the preset value is input into the control unit 103 for storage. After receiving the detection value from the sensor with analytical capacity, the control unit 103 compares the detection value with the preset value set by the user so as to determine whether to output a warning signal or not. When the user is not near the sensing component 100, a warning sound would be sent out. The user can set different warning sound effect on the smart terminal or device according to his preference. Furthermore, the user can change the preset value through the smart terminal or device (mobile phone, tablet, etc.). For example, if the preset value of the humidity is 60%, the user can change the preset value to 80%, 90% or higher by himself. When the detection value is over the preset value, the indicator light will turn on until the detection value returns to the preset value. The user can send instructions to the control unit 103 through the smart terminal or device and the control unit 103 would send out instructions directly to turn off the light. Accordingly, the user can also control the switch of the warning sound through the terminal.

With the connection between the switch unit 105 and the control unit 103, the sensing component 100 is able to control the switch of the switch unit 105. The switch unit 105 is further connected to the circuit to control the circuit by turning on and off of the switch unit 105. In various embodiment, the switch unit 105 can be a circuit breaker or a control relay connected to the circuit of the electrical components to disconnect the circuit of an external power supply, that is, to cut off the normal operation of the electrical components. The circuit breaker refers to a switch device which is able to turn on/off and carry the current under normal circuit conditions or abnormal circuit conditions within a specified period of time. The user sends the signal to the control unit 103 through a remote device, and the control unit 103 receives, analyses and processes the signal to generate a corresponding control signal. The control signal is then sent to the switch unit 105, which controls on and off of the switch unit 105, that is, to control the switch of the circuit breaker, so as to enable the remote control of the sensing component 100.

The circuit breaker is connected to the sensing component 100 and the control unit 103. It is provided that the control unit 103 can be controlled remotely, which means that the switch unit 105 can be directly disconnected by the smart terminal or device, while the control unit 103 can directly send a control signal according to the instruction from the user smart terminal or device to control the switch of the circuit breaker when the detection value of the environmental data is abnormal, so as to enable the circuit protection.

Example 2

Schematic diagrams in FIGS. 3 to 10 illustrate an intelligent socket of the present invention. The intelligent socket includes the sensing component 100, and the internal elements of the sensing component 100 are assembled on the circuit board through packaging to form a PCBA board which can be installed in the intelligent socket. The PCBA board includes a sensing unit 101, a control unit 103, a wireless transmission unit 104 and a speaker unit 102b, that is, on the circuit board there is distributed with different elements such as sensors, a MCU control chip, a wireless transmission module and a speaker, etc. These elements are communicated with each other through a circuit printed on the circuit board. The MCU control chip and the wireless transmission module are printed on the same circuit board. The sensor is set on the upper part of the circuit board, and the speaker is set on the lower part of the sensor. Due to the larger size of the sensor and the speaker, both of them are protruded above the circuit board, and the switch unit 105 is connected to the PCBA board by external wire connection. Through the reasonable layout of the components, the sensing component 100 can be installed in the intelligent socket with minimum space, so as to save the production cost.

Figure 3:
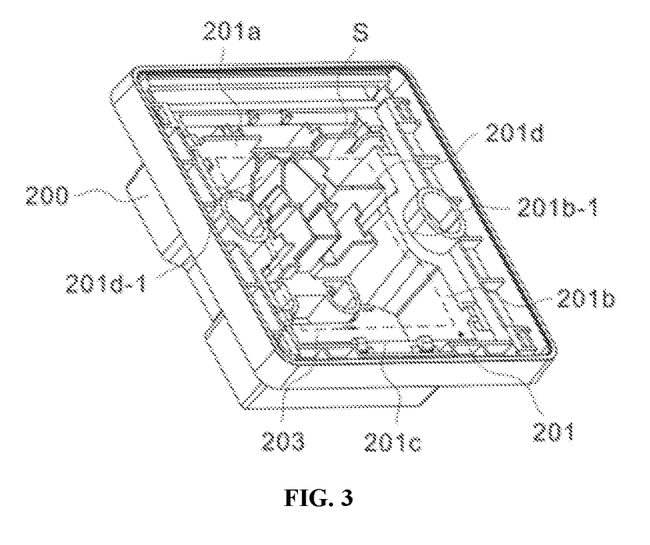
FIG. 3 is a perspective view from the bottom of the present intelligent socket.

Furthermore, the combination of the sensing component 100 and the socket can provide environmental sensing and remote control functions during the use of the socket, making the socket safer, more reliable, more convenient and more intelligent. More specifically, the intelligent socket also includes a base 200, where the base 200 has a mounting groove 201. The sensing component 100 is embedded into a confined space of the mounting groove 201. The mounting groove 201 has four side wall groove surfaces and a bottom surface to form a square cavity. The square cavity includes an upper limit plate 201a, a side limit surface 201b, and a bottom limit surface 201c to form a confined space S. The upper limit plate 201a engages with the upper side wall of the mounting groove 201. The side limit surface 201b is defined as the left side wall and right side wall of the mounting groove 201, and the bottom limit surface 201c is defined as the lower side wall of the groove. The bottom support plate 201d is arranged on the bottom surface of the mounting groove 201 and extends upward to support the PCBA board. The height difference between the bottom support plate 201d and the side limit surface 201b is not less than the thickness of PCBA board. Therefore, when the PCBA board is embedded into the confined space S, one side of the PCBA board engages with the bottom support plate 201d, the upper part of the PCBA board engages with the upper limit plate 201a, and the lower part of the PCBA board engages with the bottom limit surface 201c to confine the PCBA board in the confined space S. In various embodiment, a protruding part 201b-1 is also positioned on the side limit surface 201b, and the protruding part 201b-1 engages with the corresponding recess of the PCBA board, which can not only provide suitable bolt holes on both sides for the subsequent cover on the base 200, but also further secure the position of the PCBA board to make its installation more stable.

Figure 4:
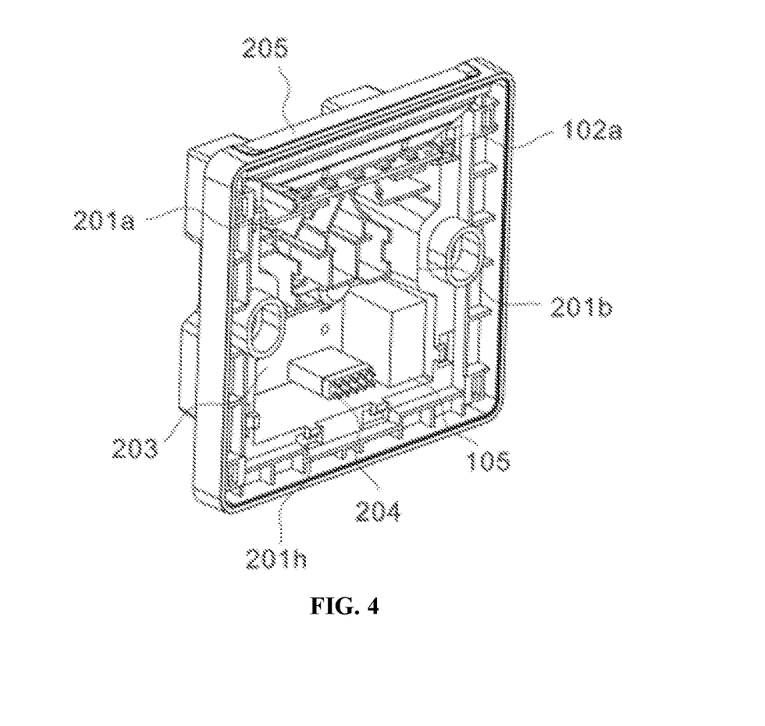
FIG. 4 is another perspective view from the bottom of the present intelligent socket.
Figure 5:
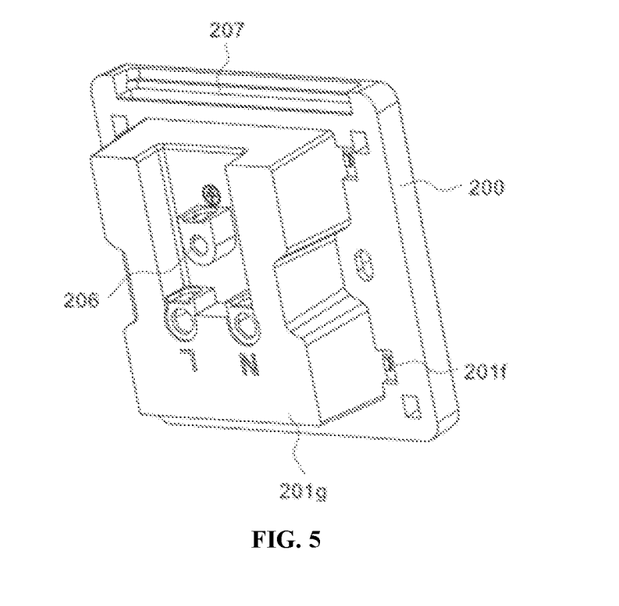
FIG. 5 is a perspective view from the top of the present intelligent socket.
Figure 6:
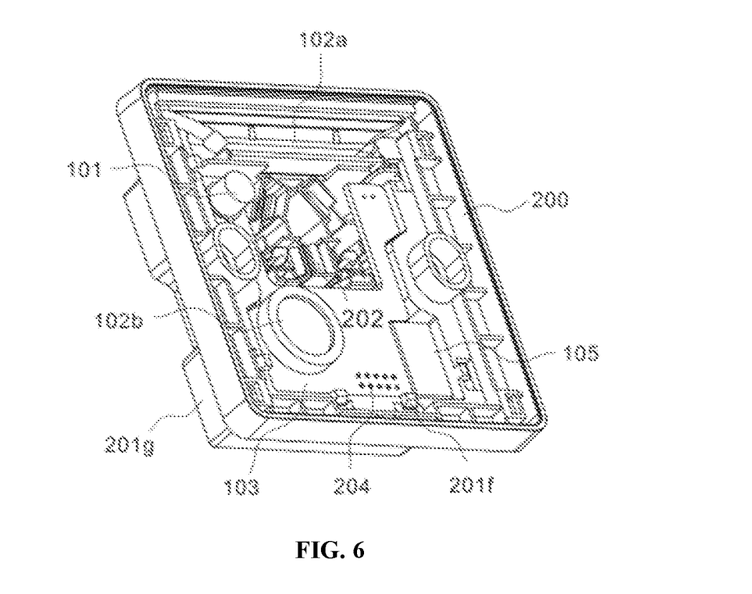
FIG. 6 illustrates the position of the power supply unit in the present intelligent socket.

Referring to the schematic diagrams in FIGS. 4 to 6, the intelligent socket also includes the conductive copper strip 202, the power supply interface 206 arranged on the back surface of the base 200, and the power supply unit 204 to supply power to the PCBA board. The conductive copper strip 202 is connected to the power supply unit 204 through the conductive plate 203, and the power supply unit 204 is connected to the sensing component 100. More specifically, a plurality of bottom support plates 201d are spaced apart from each other to form a slot 201d-1, which is set according to the requirement and shape contour of the conductive copper strip 202, for example, the conductive copper strip 202 with the requirement for three-hole or two-hole socket. Therefore, the conductive copper strip 202 is arranged in the slot 201d-1, and is connected with the power supply wire through the power supply interface 206 arranged on the base 200, which includes positive, negative and grounding ports. The public power supply wire embedded in a building is connected through the power supply interface 206 to connect with the socket 200.

In order to save space and reduce the size of the socket, the conductive plate 203 is added to connect to the conductive copper strip 202 and the power supply unit 204, respectively. The power supply unit 204 and the switch unit 105 are located on the conductive plate 203, and the power supply unit 204 is located between the PCBA board and the conductive plate 203, while the switch unit 105 is located at the right side notch of the PCBA board. The right side notch of the PCBA board and the side limit surface 201b would be able to mount the switch unit 105 in the mounting groove 201.

Because the potential of the public power supply is 220V, and the electronic components are small current components, therefore these components cannot be supplied with the public power directly. The power supply wire embedded into the wall of a building is connected to the conductive copper strip 202 through the power supply interface 206 at the back surface of the base 200. The conductive copper strip 202 transmits the electric potential to the power supply unit 204 due to the conductivity of the conductive plate 203, and then transforms it into 5V or 12V current through the power supply unit 204 to supply power to the PCBA board so that the electronics on the PCBA function properly. The PCB board is connected to the circuit breaker or control relay, and the circuit breaker is connected to the power supply wire and the power supply interface 206. By controlling the switch of the circuit breaker to cut off the connection, the power supply wire cannot supply power to the power supply interface 206, that is, there is no current flowing through the conductive copper strip 202, and thereby the electric components in contact with the conductive copper strip 202 are in open circuit, so as to enable the control of the switch of the electric components of the present invention.

The wireless transmission unit 104 and the control unit 103 are arranged on the same circuit board, i.e., the PCBA board, the speaker unit 102b and the sensing unit 101 are protruded from the surface of the circuit board, which are located below and above respectively; the indicator light unit 102a is a light strip, which is also a circuit board, positioned above the upper limit plate 201a, and is connected to the PCB board through a wire.

Corresponding to the light strip, the upper end of the base 200 is also provided with a lampshade installation slot 207 for installing the lampshade 205, so as to achieve that the lampshade 205 covers on the indicator light unit 102a, and the light emitted by the indicator light unit 102a shines on the lampshade 205. Referring to the design principle of the lampshade in the prior art, the light of the indicator light can be more uniform and soft, so as to have a better visual effect.

In various embodiment, the structure of the mounting groove 201 can be made by injection molding integrally, or a slot box 201g is used as a movable way shown in FIG. 5. The side end of the slot box 201g is provided with a hook 201f, and the bayonet 201h is correspondingly arranged on the base 200. The hook 201f is correspondingly embedded in the bayonet 201h, which can achieve the disassembly between the slot box 201g and the base 200, and facilitate the replacement of the internal components.

Figure 7:
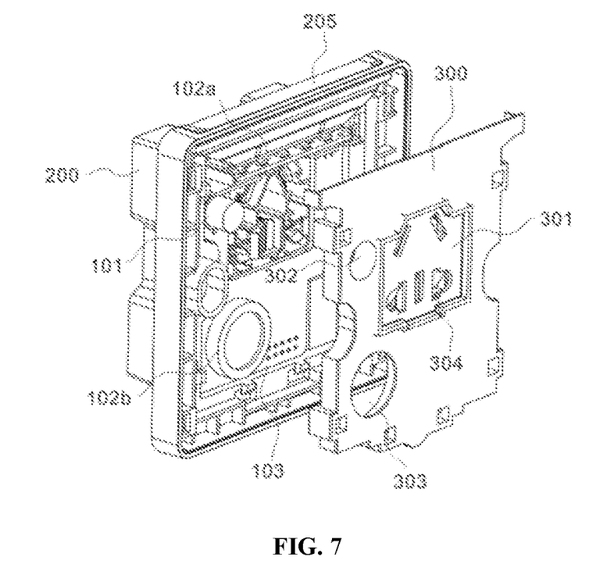
FIG. 7 is an exploded view of the middle cover of the present intelligent socket.
Figure 8:
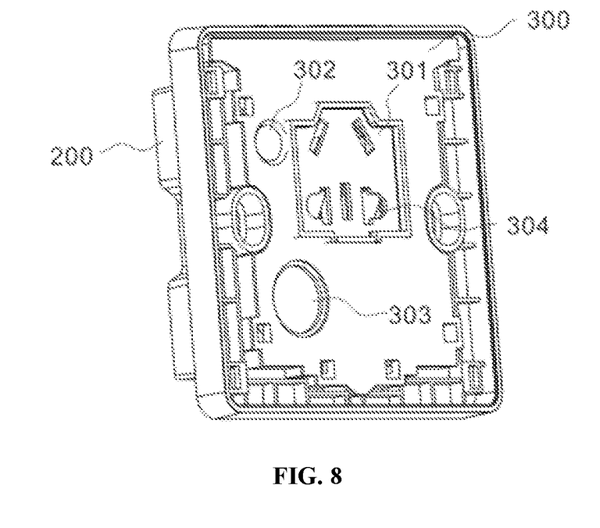
FIG. 8 is a schematic diagram of the middle cover covering the base of the present intelligent socket.

In one embodiment, the intelligent socket also includes a middle cover 300 to cover the sensing component 100 after installing on the base 200. The middle cover 300 includes a safety door 301, a sensor port 302, a speaker port 303 and a socket hole 304. More specifically, the safety door 301 is provided with a socket hole 304 for the insertion of electrical appliances, and the socket hole 304 is a combination of two holes and three holes. When the middle cover 300 is covered on the base 200, it is fastened by the hook 201f, and the speaker unit 102b is exposed through the speaker port 303, and the sensing unit 101 is exposed through the sensor port 302. The safety door 301 can be achieved by the existing socket safety door in the prior art. The sockets on the wall are all provided with safety protection covers. When the plug is inserted in use, the protection cover will automatically reverse. The plug protection cover will automatically close the socket while unplugging the plug.

Figure 9:
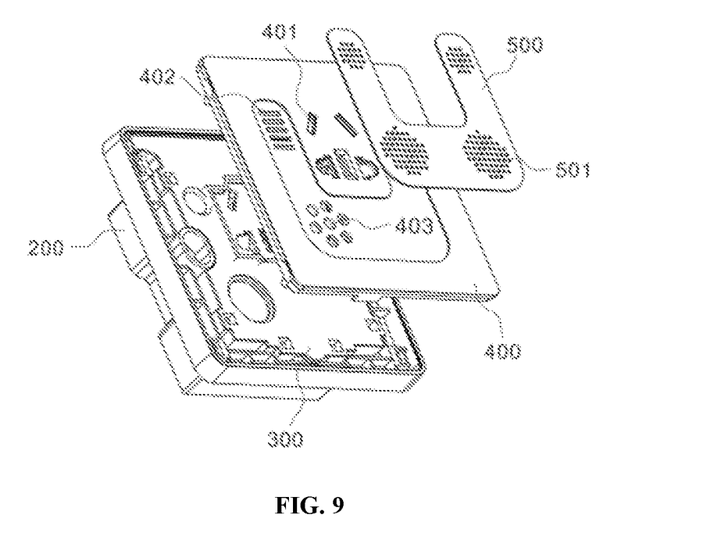
FIG. 9 is an exploded view of the present intelligent socket with a panel and a dust-proof plate.
Figure 10:
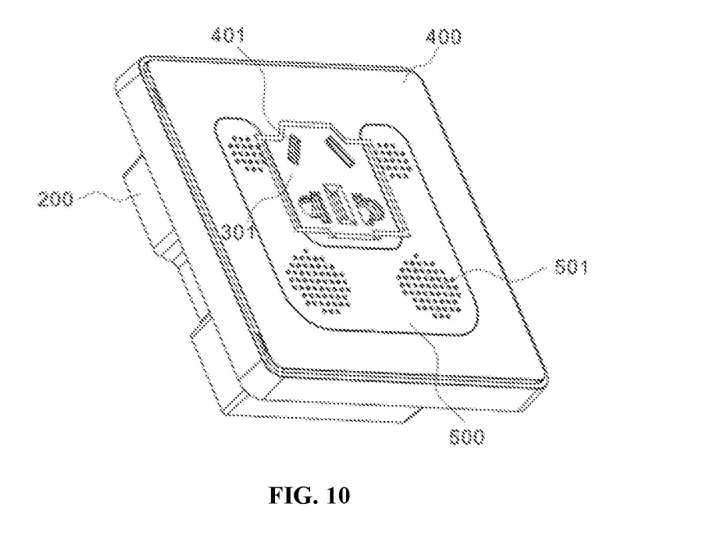
FIG. 10 is a schematic diagram depicting the present intelligent socket after assembly of different components.

Referring to the schematic diagrams in FIGS. 9 to 10, the base 200 also includes a panel 400 and a protective plate 500, wherein the panel 400 is covered on the middle cover 300 and the protective plate 500 is covered on the panel 400. More specifically, the panel 400 is provided with an outer socket 401 corresponding to the socket hole 304. The electric equipment passes through the outer socket 401 and the socket hole 304 in turn to communicate with the conductive copper strip 202, and the sensor air inlet 402 corresponding to the sensor through the sensor port 302 and the speaker inlet 403 corresponding to the speaker port 303. The protective plate 500 is further provided with a protective hole 501, corresponding to the sensor air inlet 402 and the speaker inlet 403 when the cover is closed, so as to achieve the dust-proof protection of the sensor air inlet 402 and the speaker inlet 403.

Figure 11:
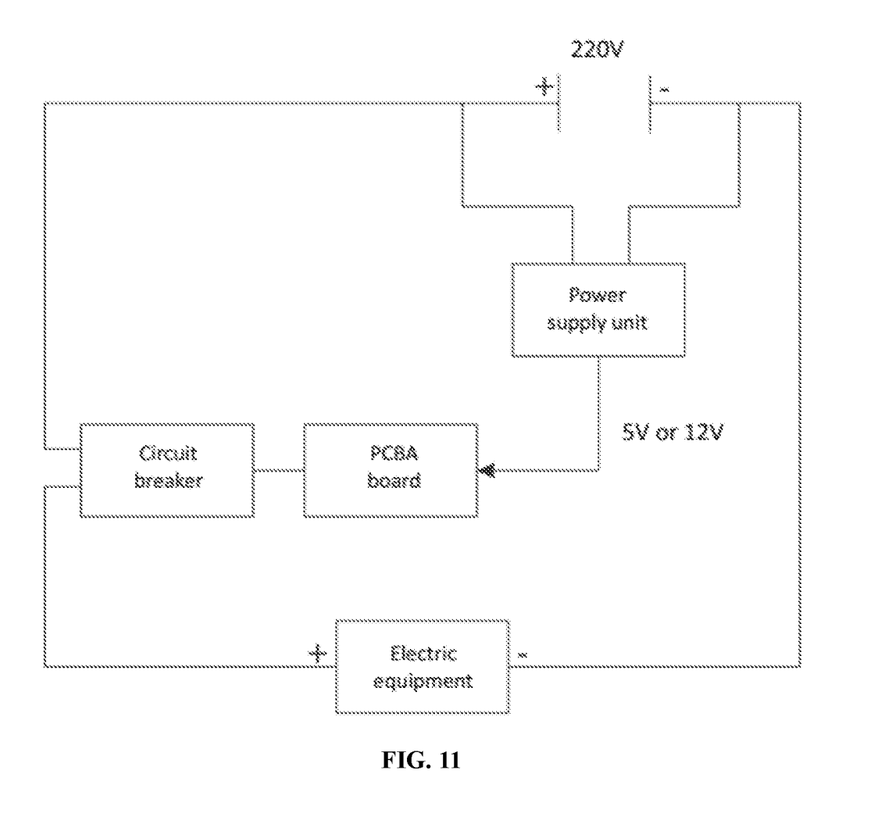
FIG. 11 is a schematic diagram depicting the working principle of the switch unit in the present intelligent socket.

Referring to the schematic diagram of FIG. 11, the principle of the switch unit 105 in the intelligent socket is illustrated. The switch unit 105, i.e., the circuit breaker or the control relay, arranged on the sensing component 100 which is able to cut off the electrical equipment connected to the socket. More specifically, the power supply wire embedded into the wall is connected to the conductive copper strip 202 through the power supply interface 206 arranged on the back of the base 200, and the electric equipment can be directly plugged into the conductive copper strip 202 through the outer socket 401 to power on. The potential of the public power supply is 220V, which is transformed into 5V or 12V current through the power supply unit to supply power to PCB board, so as to achieve the normal operation of electronic components in PCBA board. PCBA board is connected to the circuit breaker or control relay, and the circuit breaker is connected to the power supply wire and the power supply interface 206. However the circuit connecting power supply to the PCBA board is parallel to the circuit connecting the power supply wire and the power supply interface 206 such that when the power supply wire and the power supply interface 206 are in open circuit, the normal power supply to the PCB board will not be affected.

Figure 12:
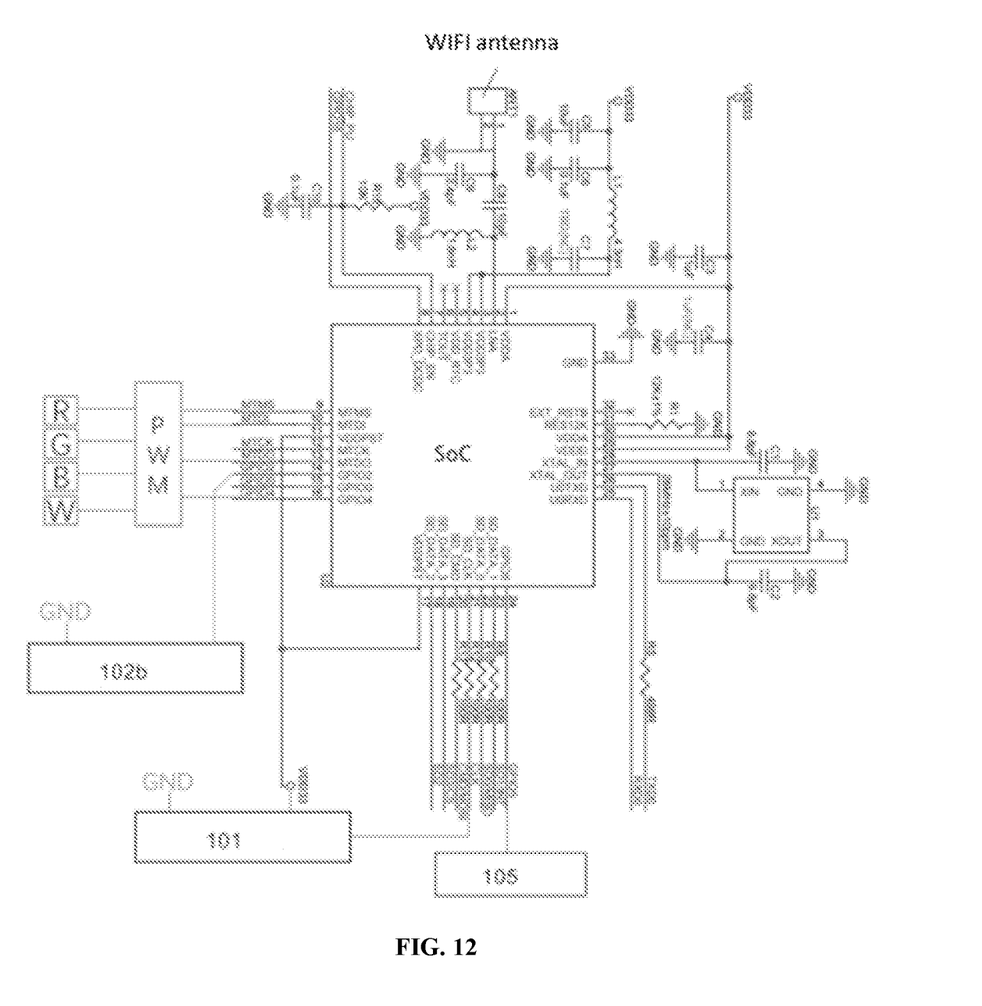
FIG. 12 is the circuit diagram of the present intelligent socket.

FIG. 12 illustrates the circuit diagram of the layout and connection of the components on the PCBA board including SoC integrated chip which integrates the MCU (i.e. control unit 103) and WI-FI™ (i.e. wireless transmission unit 104) into the chip circuit; the sensing unit 101 connected to the SoC integrated chip (i.e. sensor), indicator light unit 102a (i.e. light strip), speaker unit 102b (i.e. speaker) and switch unit 105 (i.e. circuit breaker) are also shown in the circuit diagram. Since SoC chip has no antenna function, additional antenna is needed to enhance the receiving ability, shown in the circuit diagram of WI-FI™ antenna in the figure.

UART serial port to WI-FI™ intelligent hardware includes: UART0 (U0RXD) can be used to send and receive user's own data package; UART1 (U1TXD) can be used to print out message.

The interface used by the sensor is I2C interface, and the communication mode used to determines the slave device is by addressing (each slave device has a unique address identification). The sensor transmits the collected real-time data to the control unit 103 through the I2C interface, and the control unit 103 uploads the collected data to the server through wireless transmission. When the mobile phone is connected to the Internet, it can obtain information from the server through the app.

The intelligent LED utilizes PWM interface, including 3-5 PWM interfaces to control red, blue, green (yellow, white) LED respectively. The minimum PWM duty cycle can reach 1/214, and be able to control the width of the signal.

The intelligent socket uses a common GPIO interface. Through GPIO interface for high and low level control and relay switch control to achieve the switch control function of the intelligent socket. The application is mainly composed of three modules: 220V to 5V or 12V power module, WI-FI™ module and relay control module.

In various embodiment, different sensors are installed for different scenarios, and users can select from products, such as kitchen socket (built-in smoke sensor), bathroom socket (built-in CO sensor), and the rest are purchased according to the actual needs of customers.

It has the ability to determine the data and analyze the quality of the data, which refers to the comparison with the preset value of the sensor to determine the quality of the data, so as to send out warning light or sound.

The intelligent socket is provided in the following applications:

a. Kitchen scenario (burning sensor and intelligent color light) (recommended external equipment: electric cooker, microwave oven, etc.)

Natural gas is colorless and tasteless. In order to make people recognize the leakage of natural gas at home quickly, some special substances will be added to the natural gas at home. Once the leakage occurs, it will be accompanied by a pungent smell. It will have the feeling of nausea and dizziness once suck in too much natural gas. In one embodiment, the intelligent socket has the built-in burning sensor to quickly sense the burning air leakage and warning with different light colors.

b. Bathroom scenario (CO sensor and intelligent color light) (recommended external equipment: water heater, blower, demister, etc.)

In winter, people in the bathroom is easy to have carbon monoxide poisoning. Because of the cold weather, many people often close their doors and windows when bathing. In one embodiment, the intelligent socket has the built-in CO sensor, and when the concentration exceeds the standard, it is accompanied by different colors to remind the bather to pay attention.

c. Living room scenario (sound sensor and intelligent color light) (recommended external equipment: TV, DVD and other AV equipment in the living room etc.)

According to the standard, the noise in residential areas shall not exceed 50 decibels in the daytime and 45 decibels at night. If it exceeds this standard, it will cause harm to human body. Long term noise pollution can cause serious tinnitus and deafness. In addition, it is easy to cause restlessness and other symptoms. In one embodiment, the intelligent socket has the built-in sound sensor and can timely remind people of the environmental noise through appropriate light when the environmental noise is too large.

d. Bed room scenario (temperature sensor and intelligent color light) (recommended external equipment: Dehumidifier, bedside lamp, air conditioner etc.)

The most suitable relative humidity for human body is 40%-50% at 25° C. in summer and 60%-70% at 18° C. in winter. In one embodiment, the intelligent socket has the built-in temperature and humidity sensor and can remind you with appropriate light when the temperature and humidity are abnormal, so as to keep a comfortable sleeping environment e. Study room scenario (light sensor and intelligent color light) (recommended external equipment: lamp and computer etc.)

Reading in the dark will cause eye fatigue or damage to the eyes. In one embodiment, the intelligent socket has the built-in light sensor, which can timely remind when the ambient brightness is insufficient.

The invention claimed is:

1. An intelligent socket comprising:
   a sensing component;
   a voltage transformer installed in the sensing component, wherein the voltage transformer is connected to a conductive copper strip through a conductive plate; and
   a base;
   wherein the base includes a mounting groove, and the sensing component is embedded into a confined space of the mounting groove;
   wherein a public power supply wire is connected to the conductive copper strip to provide an electricity with a first voltage;
   wherein the voltage transformer is configured to transform the electricity with the first voltage to a further electricity with second voltage, so as to provide corresponding voltage for operating functions of the sensing component, wherein the second voltage is lower than the first voltage; and
   wherein the sensing component comprises:
      one or more sensors;
      a warning unit comprising a light indicator; and
      a processor;
      wherein the sensors communicate with the processor and the warning unit communicates with the processor;
      wherein the sensors acquire at least one type of environmental data, transmit the at least one type of environmental data to the processor;
      wherein the processor transmits a control signal to the warning unit according to the received environmental data;
      wherein the warning unit receives and executes the control signal to emit warning light according to the received control signal corresponding to the received environmental data; and
      wherein the emitted warning light including combinations of light color and brightness changed with different environmental data by the control signal, so as to indicate different warnings corresponding to the different environmental data by different emitted warning lights.

2. The intelligent socket of claim 1, wherein the circuit breaker communicates with at least one electric circuit, and the switch of the electric circuit is controlled by a switch of the circuit breaker.

3. The intelligent socket of claim 1, further comprising a circuit breaker, wherein the circuit breaker communicates with the processor and the processor controls a switch of the circuit breaker.

4. The intelligent socket of claim 3, wherein the processor processes the at least one type of environmental data, generates the control signal and transmits the control signal to the circuit breaker to control a switch of the circuit breaker.

5. The intelligent socket of claim 3, further comprising a wireless transmission circuit,
   wherein
      the wireless transmission circuit communicates with the processor;
      the wireless transmission circuit transmits a message to a user smart terminal or device through wireless transmission, and
      the message includes a data transmitted from the wireless transmission circuit to the processor and a data transmitted from the processor to the wireless transmission circuit.

6. The intelligent socket of claim 5, wherein the processor receives a first signal from the user smart terminal or device, and sends a second signal to the circuit breaker to control a switch of the circuit breaker.

7. The intelligent socket of claim 4, further comprising a wireless transmission circuit,
   wherein
      the wireless transmission circuit communicates with the processor;
      the wireless transmission circuit transmits a message to a user intelligent terminal through wireless transmission, and
      the message includes a data transmitted from the wireless transmission circuit to the processor and a data transmitted from the processor to the wireless transmission circuit.

8. The intelligent socket of claim 7, wherein the processor receives a first signal from a user smart terminal or device, and sends a second signal to the circuit breaker to control a switch of the circuit breaker.

9. The intelligent socket of claim 1, wherein the light color and/or the brightness of the light indicator is controlled by a user smart terminal or device.

10. The intelligent socket of claim 9,
   wherein the warning unit further comprises a speaker unit, and
   wherein the speaker unit sends out a corresponding sound according to the received control signal corresponding to the received environmental data or the sound effect is controlled by the user smart terminal or device.

11. The intelligent socket of claim 1,
wherein the mounting groove includes an upper limit plate, a side limit surface, a bottom limit surface and a bottom support plate;
wherein the upper limit plate, the side limit surface, and the bottom limit surface form the confined space;
wherein
the bottom support plate is positioned on a bottom surface of the mounting groove and extends upward to support a printed circuit board;
the height of the bottom support plate is shorter than the height of the side limit surface;
the sensing component is positioned into the confined space and the bottom of the sensing component engages with the bottom support plate.

12. The intelligent socket of claim 11, wherein the side limit surface includes a protruding part; the protruding part engages with the sensing component.

13. The intelligent socket of claim 11,
wherein
the bottom support plate further comprises a slot;
the conductive copper strip is positioned on the slot;
the conductive plate engages with the conductive copper strip;
the voltage transformer communicates with the sensing component through the conductive copper strip and the conductive plate.

14. The intelligent socket of claim 13,
wherein
a lampshade is positioned on the base;
the lampshade is positioned on the light indicator.

* * * * *